United States Patent [19]

Nelson et al.

[11] 4,250,264
[45] Feb. 10, 1981

[54] GROWTH LIMITING MEDIA

[75] Inventors: Robert L. Nelson; James F. Drake, both of Minneapolis, Minn.

[73] Assignee: Minnesota Mining and Manufacturing Company, Saint Paul, Minn.

[21] Appl. No.: 40,914

[22] Filed: May 21, 1979

Related U.S. Application Data

[63] Continuation of Ser. No. 808,458, Jun. 21, 1977, abandoned.

[51] Int. Cl.³ .............................................. C12N 1/20
[52] U.S. Cl. ..................................... 435/253; 435/32; 435/260; 435/802
[58] Field of Search ....................... 435/29, 30, 34, 36, 435/37, 38, 39, 40, 243, 253, 260, 802, 32, 33

[56]      References Cited

U.S. PATENT DOCUMENTS 2,822,319   2/1958   Monod .................................. 435/32

OTHER PUBLICATIONS

Martin Frobisher, Fundamentals of Microbiology; 8th Ed. W. B. Saunders Co.; pp. 52–55; 1970.

Primary Examiner—Robert J. Warden
Attorney, Agent, or Firm—Cruzan Alexander; Donald M. Sell; Carolyn A. Bates

[57]            ABSTRACT

A medium for growing bacteria from an initial population to a final predetermined population where growth of the bacteria substantially subsides due to the lack of nutrient.

4 Claims, 1 Drawing Figure

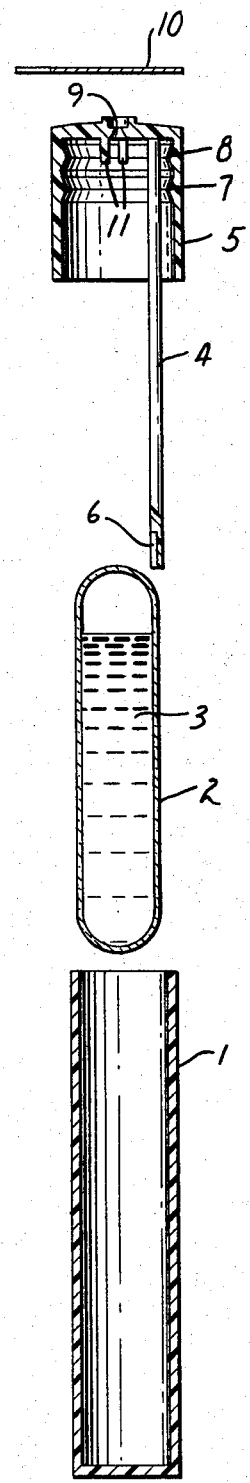

GROWTH LIMITING MEDIA

This is a continuation, of application Ser. No. 808,458 filed June 21, 1977 now abandoned.

This invention relates to a medium for growing bacteria from an initial population to another higher population, which medium then causes the bacteria to substantially cease growing due to the lack of nutrient.

In a number of procedures utilized to identify bacteria or to determine the susceptibility of the bacteria to certain antibiotics, it is necessary to have the bacteria at the beginning of the test procedure in a certain concentration range (colony forming units per ml (CFU/ml)) or the final test result will not be accurate. For example, in an article entitled "Antibiotics Susceptibility Testing by Standardized Single-Disc Method", *The American Journal of Clinical Pathology,* Vol. 45, No. 4, April, 1966, pages 493–496, and in the "Performance Standards for Antimicrobial Disc Susceptibility Tests", ASM-2, promulgated by the National Committee for Clinical Laboratory Standards, the Kirby-Bauer procedure for determining the susceptibility of rapidly growing bacteria to antibiotics and chemotherapy agents is described.

The Kirby-Bauer procedure involves growing on an agar plate colonies of bacteria obtained from a patient. A wire loop is used to pick from 4 to 5 colonies of the bacteria and introduce them into a test tube containing 4 to 5 milliliters of soybean casein digest broth. The tubes are then incubated for 2 to 8 hours to produce a bacterial suspension of moderate cloudiness. The suspension is then diluted, if necessary, with saline solution or like broth to a density visually equivalent to that of a standard prepared by adding 0.5 milliliters of 1% $BaCl_2$ to 99.5 milliliters of 1% $H_2SO_4$ (0.36 N) (0.5 McFarland standard hereinafter the McFarland standard). A plate containing Mueller-Hinton agar is then streaked with the bacterial broth suspension using a cotton swab. After the inoculum has dried, a paper disc containing an antibiotic or chemotherapeutic agent is applied to the agar. The plates are incubated. After overnight incubation the area around each disc wherein there is an absence of bacteria growth is measured. This is known as the zone of inhibition and is used to determine which antibiotic will be useful in combating the particular bacteria.

In order for the Kirby-Bauer technique to be accurate there must be approximately $1 \times 10^8$ CFU/ml included in the medium which is streaked onto the agar plate. Usually the level of growth is determined by using the visual comparison with the McFarland standard described above. The time period to reach this concentration of bacteria may vary from 2 to 8 hours depending on the bacteria. If the bacteria are allowed to grow in excess of $1 \times 10^8$ CFU/ml and become more turbid than the McFarland standard the medium must be diluted in order to be equivalent to the standard.

Another method of determining the susceptibility of bacteria to various antibiotics is called the MIC or Minimum Inhibitory Concentration test. This test is discussed in *Current Techniques for Antibiotics Susceptibility Testing* Albert Balows, © 1974, pages 77–87. This method involves preparation of a series of concentrations on an antibiotic either in a liquid or solid medium which will support the growth of a bacteria to be tested. Liquid media are conveniently dispensed in test tubes and solid media are usually poured into petri dishes. It is common practice to prepare a range of antibiotic concentrations as a series of two-fold dilutions in order to carry out the test. Each tube or petri dish is inoculated with the bacteria in question. After a period of incubation the bacterial growth or absence of growth of each antibiotic concentration is observed. In this way the minimum inhibitory concentration of the antibiotic is determined to the nearest dilution when used in a series. This is the most accurate method of determining the inhibitory concentration. However, this method did not gain popularity until recently when the laborious effect of making the dilutions was simplified. The diluted antibiotic is inoculated in the MIC test with a bacteria which is of a certain concentration, i.e., normally $10^5$ to $10^6$ CFU/ml. Broth containing bacteria equivalent of the McFarland standard, i.e., approximately $1 \times 10^8$ CFU/ml is diluted to obtain this concentration.

The aforesaid susceptibility tests as well as other tests for determining the types of bacteria or susceptibility thereof to antibiotics require that a certain predetermined amount of bacteria be utilized in the test to inoculate the plates upon which the paper disc will be placed in the case of the Kirby-Bauer test or to inoculate the diluted antibiotics in the case of the MIC test. This is required in order for the test to be accurate. If a lesser concentration of bacteria is utilized in the test, the result would indicate that the bacteria is more susceptible to the antibiotic than it would be as an actual fact. On the other hand, if the bacteria are present in a higher concentration, the test results would indicate that a higher concentration of the antibiotic would be required in order to inhibit the growth of the bacteria. Both indications would be erroneous.

In order for the aforesaid tests to be performed or tests similar thereto to be performed it is necessary for the laboratory technician to take a sample of bacteria from 4 or 5 colonies of bacteria from the agar plate upon which the bacteria has been growing and place it in a broth growth medium such as above described for 2 to 8 hours. The medium is checked periodically to determine whether or not a sufficient concentration of bacteria have grown to be equivalent to the McFarland standard. From a visual examination of the medium one will find that some medium cultures of bacteria have grown to be equivalent to the McFarland standard. Also, one may find that some cultures have not grown to the proper concentration while others have grown beyond the appropriate concentration. The former requires that the technician allow the bacteria to grow longer whereas the latter requires a dilution to bring the concentration back to that of the standard. All of these measures are tedious and time consuming.

Applicants have discovered a medium upon which bacteria can grow but which limits the concentration level to which the bacteria will indeed grow. Specifically, Applicants have discovered an aqueous medium capable of growing at least one species from two different genera of aerobic, pathogenic, rapidly growing bacteria from a beginning population to a determined ending population at which said growth of said bacteria substantially subsides due to the lack of nutrient in said medium and wherein said bacteria remain visible for at least 18 hours, said medium comprising an aqueous solution comprising a carbon source, a nitrogen source, vitamins and minerals of sufficient quantity to provide said growth and in a form usable by said bacteria for said growth.

The bacteria upon which applicants' medium is useful are aerobic bacteria, i.e., those which use oxygen to grow. The bacteria are also pathogenic in that they cause diseases and are rapidly growing in that they have a generation time of 50 minutes or less.

The medium is useful with both gram-negative as well as gram-positive aerobic, pathogenic, rapidly growing bacteria. However, the type and amount of the various ingredients in the medium are normally different for the gram-positive than for the gram-negative and the time period required to obtain the requisite concentration for the gram-positive tends to be longer than that for the gram-negative bacteria.

Applicants' growth medium will grow at least one species from two different genera of aerobic, pathogenic bacteria. Normally the medium will grow at least one species from two genera of gram-positive bacteria or at least one species from at least two genera of gram-negative bacteria. Within gram-positive aerobic bacteria, there are two genera which include the bacteria that cause most diseases for which normal bacteria and susceptibility testing is performed. These are Staphylococcus and Streptococcus. If the medium will grow species from each of these two genera then it allows one to merely test the bacteria to determine whether it is gram-positive or negative using a gram stain test. If the bacteria is gram-positive the medium which grow the gram-positive bacteria is used and the medium will grow the bacteria to the level desired such as to the equivalent of the McFarland standard.

If the bacteria is determined to be gram-negative using the gram stain test, the bacteria could be from a much larger number of genera. Sixteen genera represent the bacteria found to be the cause of 99% of illnesses caused by gram-negative, aerobic bacteria. These gram-negative genera include: Escherichia, Shigella, Edwardsiella, Salmonella, Arizona, Citrobacter, Klebsiella, Enterobacter, Serratia, Proteus, Providencia, Yersinia, Pseudomonas, Acinetobacter, Moraxella and Pasteurella.

The medium grows the bacteria from a certain population which will normally be described in terms of CFU as above defined and will normally be referenced to the population in a certain volume of medium, i.e., CFU/ml. The beginning concentration can range as low as 1 CFU but will normally be, and is preferable, at least $5 \times 10^6$ CFU/ml.

Starting with a lower initial population or concentration will not cause the medium to grow the bacteria to a significantly different final population or concentration than with a higher starting concentration but will affect the time it takes for the final concentration to be reached. The final concentration to which the bacteria grow is referred to as the stationary phase.

As above discussed the time to reach a concentration equivalent to the McFarland standard varies according to the test procedure from 2 to 8 hours with most bacteria taking at least 5 to 6 hours to reach that concentration. Applicants' media preferably reaches the final concentration or stationary phase within 5 hours. However, a feature of applicants' medium is that if the bacteria reaches the stationary phase in 2 hours it will remain there even if the technician does not check the medium for 5 hours and no dilution will be required to obtain a concentration equivalent to the McFarland standard.

When the stationary phase or final concentration is reached with applicants' medium the growth of the bacteria substantially subsides. This is due to there being an exhaustion of at least one nutrient critical to the continued growth of the bacteria and not to the formation of toxic byproducts by the bacteria which stop growth and can cause the population to decrease substantially. With the standard media used prior to the present invention and described in the Kirby-Bauer procedure, the population of the bacteria which would be reached in order for growth to subside would be determined by toxic byproducts of the bacteria. This population of bacteria is above the McFarland standard which is described in the Kirby-Bauer procedure.

The final concentration or maximum stationary phase is obtained because of exhaustion of one or more nutrients. At that point the viable CFU/ml count levels off and remains substantially unchanged for at least about 18 hours. The bacteria remain viable for a period of time useful for carrying out the various tests to be performed thereon for example those described above. Normally the time period for such viability is at least 18 hours.

The final concentration which is desired to be reached with most bacteria will be between $6 \times 10^7$ to 3.0 to $10^8$ CFU/ml. This is equivalent to the 0.5 McFarland standard. The medium can be modified to reach different desired concentration levels.

The medium will contain different types and amounts of ingredients depending upon the final concentration of bacteria being grown. In all cases a carbon and nitrogen source are present which provide carbon and nitrogen in a form useful by the bacteria for growth. Normally vitamins and minerals are also present. However, as noted, the amount of one or more of these ingredients is limited to cause the bacteria to reach a final predetermined concentration and substantially cease growing.

For the gram-negative bacteria, a preferred medium comprises about 0.42 to about 0.70 milligrams of carbon per milliliter of medium. The carbon is in a form useful by the bacteria for growth. This form has been found to be the form which carbon is present in peptone or a similar form. The preferred medium also comprises 0.09 to 0.15 milligrams of nitrogen per milliliter of medium in a form similar to the nitrogen present in peptone. The preferred medium has a pH from about 7 to 8. With proteose peptone the range for carbon is from about 0.16 to about 0.27 milligrams of carbon per milliliter of medium, the nitrogen is 0.035 to 0.056 milligrams nitrogen per milliliter of medium and the carbon and nitrogen are as found in proteose peptone or a form similar thereto. A typical analysis of the peptone and proteose peptone is set forth below:

| Percent | Peptone | Proteose Peptone |
|---|---|---|
| Total Nitrogen | 16.16 | 14.37 |
| Primary Proteose N | 0.06 | 0.60 |
| Secondary Proteose N | 0.68 | 4.03 |
| Peptone N | 15.38 | 9.74 |
| Ammonia N | 0.04 | 0.00 |
| Free Amino | 3.20 | 2.66 |
| Amide N | 0.49 | 0.94 |
| Mono-amino N | 9.42 | 7.61 |
| Di-amino N | 4.07 | 4.51 |
| Tryptophane | 0.29 | 0.51 |
| Tyrosine | 0.98 | 2.51 |
| Crystine | 0.22 | 0.56 |
| Organic Sulfur | 0.33 | 0.60 |
| Inorganic Sulfur | 0.29 | 0.04 |
| Phosphorus | 0.22 | 0.47 |
| Chlorine | 0.27 | 3.95 |
| Sodium | 1.08 | 2.84 |

| -continued | | |
|---|---|---|
| Potassium | 0.22 | 0.70 |
| Calcium | 0.058 | 0.137 |
| Magnesium | 0.056 | 0.118 |
| Manganese | nil | 0.0002 |
| Iron | 0.0033 | 0.0056 |
| Ash | 3.53 | 9.61 |
| Ether Soluble Extract | 0.37 | 0.32 |
| Reaction, pH | 7.0 | 6.8 | pH 1% solution in distilled water after autoclaving 15 minutes at 121° C.

The preferred formulation contains the vitamins and minerals found in peptone or proteose peptone. Two specifically preferred formulations which have been found to be useful in growing the gram-negative bacteria to a final concentration of from $6 \times 10^7$ to $3 \times 10^8$ CFU/ml in less than 5 hours comprises a mixture of 1000 ml of water containing 0.8 gram peptone or 0.3 gram proteose peptone, 0.03 gram dextrose, 2.5 gram dipotassium phosphate, 1.25 gram monopotassium phosphate and 5.0 grams sodium chloride. The phosphates are added as a buffer material to maintain the composition at a pH of approximately 7.0. Buffering is necessary with certain of the bacteria. The aforesaid two formulations provide a medium upon which species from most of the genera of the gram-negative, aerobic, pathogenic bacteria can grow to the above described CFU/ml ranges within 5 hours.

As noted the preferred carbon and nitrogen sources are peptone and proteose peptone for the gram-negative bacteria. Neopeptone, tryptone and polypeptone can also be used but it has been found that these do not produce growth to the levels of the McFarland standard within the same time frame and with some of the bacteria within this group do not provide the appropriate nutrients to grow the bacteria to any significant degree. Therefore, these materials are useful for more limited numbers of bacteria. However, combinations of such materials with peptone or proteose peptone can be used to provide a medium useful with a larger number of bacteria.

A preferred medium for use with the gram-positive bacteria comprises a solution of 1000 ml of water containing 1.7 grams trypticase, 0.3 gram phytone, 0.25 gram dextrose, 0.5 gram sodium chloride and 0.25 gram dipotassium phosphate.

All the various media are used by inoculating the medium with the bacteria and incubating the medium for 2 to 8 hours.

A device for such inoculation is described below with reference to the FIGURE. This device is the subject of a separate patent application filed concurrently herewith.

In the following examples, reference will be made to the use of a growing device containing medium which is made for use in picking up bacteria from growing colonies of bacteria and for providing medium for growing the bacteria. The concentration of the bacteria as removed from 4 to 5 colonies from which the bacteria are obtained is from $5 \times 10^6$ to $1 \times 10^8$ CFU's per milliliter.

The device comprises a sleeve 1 which is made of a deformable material such as polypropylene, polyamide, cellulose acetate butyrate or various polyesters. The sleeve is transparent, closed on one end and contains within it a frangible ampoule 2 containing the growth medium 3 of the present invention. In use the deformable sleeve 1 is squeezed by means of a crushing device (not shown) and glass ampoule 2 breaks allowing the medium 3 to mix with and grow the bacteria which are introduced into the sleeve 1 by means of wand 4. Wand 4 is affixed to cap 5 and contains within it a tapered groove 6 which allows for pick-up of bacteria by means of capillary action, i.e., when the wand is pushed into a colony of bacteria the bacteria move up the groove 6 and a majority of the air previously occupying the groove is pushed out of the top of the groove 6. Cap 5 contains within it two ridges 7 and 8 which provide a tight seal against sleeve 1 but does allow for removal of cap 5 from sleeve 1. Cap 5 also contains hole 9 which allows the bacteria after growth to be expressed from the sleeve 1 through deformation of sleeve 1. Hole 9 is covered by adhesive tape 10 which covers the hole 9 until it is desired to exude the grown bacteria and media 3 from the sleeve 1. Cap 5 also contains protrusions 11 which are three in number and prevent the glass from glass ampoule 2 from plugging hole 9 during the exudation process.

In the examples below the growing devices were filled by placing 0.6 ml of medium 3 in the glass ampoule 2 and heat sealing the ampoule 2. The ampoules were steam sterilized for 10 minutes at 121° C. The sleeve 1, cap 5 and tape 10 were ethylene oxide gas sterilized for 3 hours and 100° C. and then aerated for 8 hours. The sealed and sterilized glass ampoules were asceptically added to the sleeves; the caps were attached and the tapes were pressed into place. The growing devices were then ready for use.

In the following examples the following materials and bacteria are references. The source is set forth below:

Tryptone, an enzymatic hydrolysate of casein, Difco, Inc., Detroit, Mich.

Peptone, an enzymatic hydrolysate of casein, Difco, Inc., Detroit, Mich.

Dextrose, Difco, Inc., Detroit, Mich.

Polypeptone, an enzymatic hydrolysate of casein and animan tissue, Bioquest, Inc., Baltimore, Md.

Neopeptone, an enzymatic hydrolysate of protein, Difco, Inc., Detroit, Mich.

Proteose peptone, an enzymatic hydrolysate of protein, Difco, Inc., Detroit, Mich.

Phytone, an enzymatic hydrolysate of soybeans, Bioquest, Inc., Baltimore, Md.

*Salmonella typhimurium*, American Type Culture Collection, (ATCC) No. 19028

Shigella Sonnei, (ATCC 25331)

*Enterobacter cloacae* (ATCC 23355) and St. Paul Ramsey Hospital, St. Paul, Minn.

*Klebsiella pneumoniae*, (ATCC 23357) and St. Paul Ramsey Hospital, St. Paul, Minn.

*Proteus vulgaris* (ATCC 6380)

*Proteus mirabilis*, St. John's Hospital, St. Paul, Minn. and St. Paul Ramsey Hospital, St. Paul, Minn.

*Serratia marcescens* (ATCC 8100) and St. Paul Ramsey Hospital, St. Paul, Minn.

Providencia species, University of Minnesota, Minneapolis, Minn.

Citrobacter species, University of Minnesota, Minneapolis, Minn.

Edwardsiella, University of Minnesota, Minneapolis, Minn.

Arizona, University of Minnesota, Minneapolis, Minn.

Yersinia, University of Minnesota, Minneapolis, Minn.

*Pseudomonas aeruginosa* (ATCC 27853) St. Paul Ramsey Hospital, St. Paul, Minn.

*Escherichia coli* (ATCC 25922) and St. Paul Ramsey Hospital, St. Paul, Minn.

*Acinetobacter calcoaceticus,* St. Paul Ramsey Hospital, St. Paul, Minn.

*Proteus morganii,* St. Paul Ramsey Hospital, St. Paul, Minn.

*Enterobacter aerogenes,* St. Paul Ramsey Hospital, St. Paul, Minn.

*Pasteurella* (species), St. Paul Ramsey Hospital, St. Paul, Minn.

CDC Group II F, St. Paul Ramsey Hospital, St. Paul, Minn.

*Moraxella,* St. Paul Ramsey Hospital, St. Paul, Minn.

*Citrobacter freundii,* St. Paul Ramsey Hospital, St. Paul, Minn.

Trypticase, an enzymatic hydrolysate of casein, Bioquest, Inc., Baltimore, Md.

EXAMPLE 1

The following materials were dissolved in 1000 milliliters of deionized water and steam sterilized at 121° C. for 15 minutes:

0.8 gram Peptone
0.03 gram Dextrose
2.5 gram Dipotassium phosphate
1.25 gram Monopotassium phosphate
5.0 grams Sodium chloride Solutions of media containing 0.2 gram peptone and 1.6 grams peptone were also prepared. Growing devices were then prepared using each of the media. Utilizing the wand 4 of the growing device bacteria were picked from 4 to 5, 18 to 24 hour old bacterial colonies of the various bacteria set forth in the table below. Five growing devices were used for each bacteria to obtain a mean of 5 samples for each bacteria. Fourteen different bacteria were tested; thus, there were 70 growing devices utilized in the test for each of the 3 media. Each growing device was vortexed, i.e., mixed for 10 seconds and incubated at 35° C. Viable bacteria counts were performed at 0, 4, 5, and 6 hours. The results are set forth in the table below:

TABLE 1

| Bacteria | Time | Count ($\times 10^7$ CFU/ml) 0.2g | 0.8g | 1.6g |
|---|---|---|---|---|
| *Escherichia coli* | 0 hours | 1.6 | 1.44 | 2.4 |
| | 4 hours | 0.4 | 5.2 | 11.6 |
| | 5 hours | 3.7 | 10.2 | 14.8 |
| | 6 hours | 1.3 | 7.6 | 15.4 |
| *Shigella sonnei* | 0 hours | 4.2 | 3.62 | 1.2 |
| | 4 hours | 5.7 | 14.4 | 15.8 |
| | 5 hours | 8.1 | 17.0 | 19.8 |
| | 6 hours | 6.0 | 12.2 | 21.0 |
| *Klebsiella pneumoniae* | 0 hours | 2.6 | 2.86 | 2.6 |
| | 4 hours | 5.3 | 13.4 | 11.6 |
| | 5 hours | 4.9 | 13.6 | 13.6 |
| | 6 hours | 4.9 | 12.0 | 16.0 |
| *Enterobacter cloacae* | 0 hours | 5.3 | 4.4 | 3.9 |
| | 4 hours | 9.4 | 17.0 | 17.4 |
| | 5 hours | 9.2 | 19.0 | 26.0 |
| | 6 hours | 9.4 | 19.6 | 38.6 |
| *Providencia species* | 0 hours | 7.3 | 6.14 | 9.1 |
| | 4 hours | 11.6 | 22.2 | 30.2 |
| | 5 hours | 13.2 | 27.4 | 38.6 |
| | 6 hours | 13.2 | 22.8 | 39.8 |
| *Proteus mirabilis* | 0 hours | 4.2 | 4.66 | 5.4 |
| | 4 hours | 8.9 | 21.4 | 21.4 |
| | 5 hours | 8.6 | 19.8 | 33.2 |
| | 6 hours | 9.7 | 24.0 | 37.2 |
| *Salmonella typhimurium* | 0 hours | 2.4 | 2.32 | 3.8 |
| | 4 hours | 6.6 | 16.4 | 27.8 |

TABLE 1-continued

| Bacteria | Time | Count ($\times 10^7$ CFU/ml) 0.2g | 0.8g | 1.6g |
|---|---|---|---|---|
| | 5 hours | 7.1 | 16.4 | 31.0 |
| | 6 hours | 6.8 | 19.0 | 33.2 |
| *Pseudomonas aeruginosa* | 0 hours | 1.0 | 0.7 | 0.8 |
| | 4 hours | 5.6 | 14.6 | 11.4 |
| | 5 hours | 3.6 | 16.6 | 18.6 |
| | 6 hours | 5.3 | 26.4 | 29.2 |
| *Citrobacter species* | 0 hours | 3.8 | 31.0 | 6.6 |
| | 4 hours | 9.2 | 20.8 | 21.0 |
| | 5 hours | 9.3 | 20.8 | 30.6 |
| | 6 hours | 12.6 | 31.4 | 32.6 |
| *Arizona* | 0 hours | 1.1 | 1.46 | 2.0 |
| | 4 hours | 41. | 15.2 | 16.0 |
| | 5 hours | 4.9 | 16.0 | 21.8 |
| | 6 hours | 4.9 | 17.6 | 26.2 |
| *Edwardsiella* | 0 hours | 2.2 | 2.98 | 1.9 |
| | 4 hours | 2.3 | 6.04 | 8.3 |
| | 5 hours | 2.5 | 6.02 | 8.8 |
| | 6 hours | 2.4 | 5.9 | 10.5 |
| *Yersinia* | 0 hours | 3.3 | 3.02 | 3.7 |
| | 4 hours | 5.0 | 9.9 | 16.0 |
| | 5 hours | 5.4 | 11.5 | 19.2 |
| | 6 hours | 6.7 | 13.0 | 21.2 |
| *Serrati marcescens* | 0 hours | 1.1 | 1.62 | 1.1 |
| | 4 hours | 5.2 | 10.0 | 14.0 |
| | 5 hours | 6.3 | 16.8 | 17.8 |
| | 6 hours | 6.8 | 26.3 | 23.4 |
| *Proteus vulgaris* | 0 hours | 1.7 | 1.36 | 0.5 |
| | 4 hours | 6.5 | 19.36 | 19.2 |
| | 5 hours | 6.3 | 23.2 | 31.4 |
| | 6 hours | 7.3 | 22.0 | 34.5 |

EXAMPLE 2

Example 1 was repeated except that polypeptone was substituted for peptone. The results are set forth in the table below:

TABLE 2

| Bacteria | Time | (Count $\times 10^7$ CFU/ml) 0.2g | 0.8g | 1.6g |
|---|---|---|---|---|
| *Escherichia coli* | 0 hours | 1.4 | 0.8 | 1.1 |
| | 4 hours | 7.8 | 9.8 | 6.8 |
| | 5 hours | 6.0 | 5.5 | 5.5 |
| | 6 hours | 6.7 | 7.9 | 7.9 |
| *Shigella sonnei* | 0 hours | 1.7 | 1.68 | 2.8 |
| | 4 hours | 7.1 | 9.98 | 10.6 |
| | 5 hours | 6.4 | 9.88 | 11.4 |
| | 6 hours | 8.0 | 11.4 | 11.0 |
| *Klebsiella pneumoniae* | 0 hours | 3.0 | 3.64 | 3.3 |
| | 4 hours | 6.9 | 4.78 | 7.1 |
| | 5 hours | 7.0 | 7.3 | 8.0 |
| | 6 hours | 7.8 | 12.6 | 9.5 |
| *Enterobacter cloacae* | 0 hours | 4.2 | 3.2 | 1.8 |
| | 4 hours | 16.2 | 19.0 | 8.1 |
| | 5 hours | 15.8 | 12.8 | 13.2 |
| | 6 hours | 11.6 | 13.6 | 16.8 |
| *Providencia species* (inoculum error) | 0 hours | — | — | — |
| | 4 hours | — | — | — |
| | 5 hours | — | — | — |
| | 6 hours | — | — | — |
| *Proteus mirabilis* | 0 hours | 0.46 | 0.46 | 0.34 |
| | 4 hours | 2.7 | 3.86 | 3.6 |
| | 5 hours | 7.6 | 14.6 | 13.0 |
| | 6 hours | 7.5 | 10.6 | 11.4 |
| *Salmonella typhimurium* | 0 hours | 1.3 | 1.4 | 0.91 |
| | 4 hours | 6.8 | 6.9 | 7.4 |
| | 5 hours | 10.0 | 11.8 | 10.7 |
| | 6 hours | 9.0 | 14.1 | 11.0 |
| *Pseudomonas aeruginosa* | 0 hours | 5.8 | 7.7 | 5.6 |
| | 4 hours | 8.0 | 8.3 | 11.0 |
| | 5 hours | — | 22.2 | 24.8 |
| | 6 hours | 7.5 | 20.3 | 23.6 |
| *Citrobacter species* | 0 hours | 15.4 | 21.6 | 34.2 |
| | 4 hours | 16.6 | 22.4 | 22.2 |
| | 5 hours | 14.8 | 31.4 | 25.6 |
| | 6 hours | 15.2 | 27.2 | 30.4 |

TABLE 2-continued

| Bacteria | Time | Count × 10⁷ CFU/ml 0.2g | 0.8g | 1.6g |
|---|---|---|---|---|
| Arizona | 0 hours | 3.7 | 4.0 | 3.2 |
| | 4 hours | 5.3 | 6.6 | 5.6 |
| | 5 hours | 6.6 | 13.2 | 12.5 |
| | 6 hours | 7.0 | 20.8 | 17.2 |
| Edwardsiella | 0 hours | No growth | | |
| | 4 hours | No growth | | |
| | 5 hours | No growth | | |
| | 6 hours | No growth | | |
| Yersinia | 0 hours | 4.4 | 2.85 | 5.7 |
| | 4 hours | 4.4 | 5.0 | 10.7 |
| | 5 hours | 8.0 | 9.73 | 17.2 |
| | 6 hours | 8.6 | 11.0 | 18.6 |
| Serratia marcescens | 0 hours | 4.4 | 4.6 | 4.1 |
| | 4 hours | 13.6 | 11.1 | 8.8 |
| | 5 hours | 15.2 | 14.4 | 10.1 |
| | 6 hours | 15.4 | 15.0 | 13.6 |
| Proteus vulgaris | 0 hours | 4.5 | 2.64 | 1.4 |
| | 4 hours | 6.9 | 7.92 | 4.2 |
| | 5 hours | 15.5 | 15.4 | 11.3 |
| | 6 hours | 16.5 | 18.0 | 15.3 |

EXAMPLE 3

Example 1 was repeated except that neopeptone was substituted for the peptone. The results are set forth in the table below:

TABLE 3

| Bacteria | Time | Count (× 10⁷ CFU/ml) 0.2g | 0.8g | 1.6g |
|---|---|---|---|---|
| Escherichia coli | 0 hours | 0.84 | 1.0 | 0.55 |
| | 4 hours | 0.54 | 0.6 | 0.38 |
| | 5 hours | 1.8 | 1.96 | 1.1 |
| | 6 hours | 1.3 | 4.0 | 3.0 |
| Shigella sonnei | 0 hours | 1.8 | 0.8 | 0.79 |
| | 4 hours | 3.3 | 2.3 | 1.0 |
| | 5 hours | 4.6 | 6.2 | 4.2 |
| | 6 hours | 6.3 | 6.1 | 4.0 |
| Klebsiella pneumoniae | 0 hours | 0.2 | 0.13 | 0.1 |
| | 4 hours | 3.7 | 2.5 | 4.0 |
| | 5 hours | 7.2 | 2.5 | 8.0 |
| | 6 hours | 5.3 | 5.8 | 8.2 |
| Enterobacter cloacae | 0 hours | | No growth | |
| | 4 hours | | No growth | |
| | 5 hours | | No growth | |
| | 6 hours | | No growth | |
| Providencia species | 0 hours | 0.4 | — | 0.2 |
| | 4 hours | 0.7 | — | 0.6 |
| | 5 hours | 1.4 | — | 0.7 |
| | 6 hours | 1.9 | — | 1.8 |
| Proteus mirabilis | 0 hours | 2.0 | 1.0 | 4.2 |
| | 4 hours | 6.3 | 8.5 | 6.8 |
| | 5 hours | 10.0 | 17.6 | 16.0 |
| | 6 hours | 10.5 | 21.8 | 22.2 |
| Salmonella typhimurium | 0 hours | 3.3 | 2.48 | 2.6 |
| | 4 hours | 7.2 | 8.92 | 8.0 |
| | 5 hours | 13.2 | 17.2 | 19.0 |
| | 6 hours | 12.6 | 16.6 | 18.0 |
| Pseudomonas aeruginosa | 0 hours | 0.2 | 0.16 | 0.24 |
| | 4 hours | 1.8 | 5.9 | 4.9 |
| | 5 hours | 5.3 | 9.5 | 9.6 |
| | 6 hours | 7.2 | 18.0 | 16.0 |
| Citrobacter species | 0 hours | 5.4 | 7.62 | 13.0 |
| | 4 hours | 7.4 | 7.44 | — |
| | 5 hours | 12.2 | 24.6 | 27.2 |
| | 6 hours | 15.6 | 30.2 | 31.4 |
| Arizona | 0 hours | 3.4 | 3.0 | 2.6 |
| | 4 hours | 6.3 | 6.6 | 7.6 |
| | 5 hours | 7.9 | 13.0 | 11.8 |
| | 6 hours | 9.8 | 16.4 | 17.4 |
| Yersinia | 0 hours | 4.9 | 6.24 | 6.0 |
| | 4 hours | 6.0 | 10.7 | 10.8 |
| | 5 hours | 9.7 | 15.5 | 16.0 |
| | 6 hours | 10.4 | 20.6 | 21.0 |
| Edwardsiella | 0 hours | | No data | |
| | 4 hours | | No data | |

TABLE 3-continued

| Bacteria | Time | Count (× 10⁷ CFU/ml) 0.2g | 0.8g | 1.6g |
|---|---|---|---|---|
| | 5 hours | | No data | |
| | 6 hours | | No data | |
| Serratia marcescens | 0 hours | 3.5 | 3.16 | 5.1 |
| | 4 hours | 8.7 | 10.1 | 9.8 |
| | 5 hours | 11.3 | 11.6 | 12.3 |
| | 6 hours | 9.7 | 12.7 | 12.8 |
| Proteus vulgaris | 0 hours | 2.4 | 3.56 | 2.0 |
| | 4 hours | 5.5 | 12.5 | 8.1 |
| | 5 hours | 8.6 | 23.8 | 16.4 |
| | 6 hours | 10.7 | 28.4 | 23.2 |

EXAMPLE 4

Example 1 was repeated except that tryptone was substituted for peptone. The results are set forth in the table below:

TABLE 4

| Bacteria | Time | Count (× 10⁷ CFU/ml) 0.2g | 0.8g | 1.6g |
|---|---|---|---|---|
| Escherichia coli | 0 hours | 3.5 | 3.9 | 2.1 |
| | 4 hours | 12.2 | 17.8 | 13.5 |
| | 5 hours | 13.2 | 22.8 | 18.4 |
| | 6 hours | 13.0 | 25.2 | 23.2 |
| Shigella sonnei | 0 hours | 1.0 | 0.4 | 0.33 |
| | 4 hours | 6.3 | 11.0 | 10.0 |
| | 5 hours | 7.1 | 16.0 | 16.0 |
| | 6 hours | 8.2 | 21.3 | 22.3 |
| Klebsiella pneumoniae | 0 hours | 5.9 | 5.32 | 4.7 |
| | 4 hours | 13.2 | 14.2 | 16.2 |
| | 5 hours | 14.0 | 15.8 | 15.4 |
| | 6 hours | 13.0 | 19.6 | 19.4 |
| Enterobacter cloacae | 0 hours | 8.7 | 7.08 | 10.6 |
| | 4 hours | 15.4 | 29.0 | 24.2 |
| | 5 hours | 15.2 | 34.2 | 33.4 |
| | 6 hours | 17.4 | 40.6 | 39.4 |
| Providencia species | 0 hours | 3.2 | 3.62 | 3.9 |
| | 4 hours | 8.2 | 16.4 | 17.0 |
| | 5 hours | 8.2 | 22.4 | 22.2 |
| | 6 hours | 5.8 | 24.6 | 27.4 |
| Proteus mirabilis | 0 hours | 3.3 | 2.08 | 3.3 |
| | 4 hours | 11.8 | 16.2 | 19.8 |
| | 5 hours | 11.1 | 21.6 | 19.0 |
| | 6 hours | 13.0 | 26.2 | 24.0 |
| Salmonella typhimurium | 0 hours | 1.1 | 1.56 | 1.0 |
| | 4 hours | 7.5 | 15.6 | 11.6 |
| | 5 hours | 8.0 | 21.4 | 13.8 |
| | 6 hours | 10.6 | 27.6 | 19.2 |
| Pseudomonas aeruginosa | 0 hours | 3.4 | 2.52 | 2.9 |
| | 4 hours | 10.0 | 11.0 | 11.6 |
| | 5 hours | 11.0 | 10.4 | 13.0 |
| | 6 hours | | | |
| Citrobacter species | 0 hours | 3.3 | 2.66 | 2.4 |
| | 4 hours | 16.6 | 15.8 | 17.2 |
| | 5 hours | 16.8 | 25.4 | 20.4 |
| | 6 hours | 17.0 | 34.4 | 27.7 |
| Arizona | 0 hours | 1.4 | 1.0 | 0.66 |
| | 4 hours | 5.5 | 6.2 | 6.3 |
| | 5 hours | 5.7 | 12.0 | 10.2 |
| | 6 hours | 6.4 | 17.3 | 14.2 |
| Edwardsiella | 0 hours | 0.78 | 0.85 | 1.6 |
| | 4 hours | 2.3 | 1.9 | 3.4 |
| | 5 hours | 3.1 | 2.3 | 3.9 |
| | 6 hours | 2.9 | 2.8 | 4.8 |
| Yersinia | 0 hours | 2.0 | 1.58 | 2.7 |
| | 4 hours | 5.1 | 5.8 | 10.0 |
| | 5 hours | 6.1 | 8.42 | 13.6 |
| | 6 hours | 7.1 | 12.8 | 18.3 |
| Serratia marcescens | 0 hours | 3.2 | 4.98 | 3.0 |
| | 4 hours | 16.6 | 20.8 | 15.6 |
| | 5 hours | 19.2 | 25.4 | 21.4 |
| | 6 hours | 23.2 | 29.8 | 25.8 |
| Proteus vulgaris | 0 hours | 1.46 | 1.1 | 1.0 |
| | 4 hours | 8.0 | 16.2 | 13.3 |
| | 5 hours | 10.0 | 16.5 | 18.0 |

TABLE 4-continued

| Bacteria | Time | Count ($\times 10^7$ CFU/ml) | | |
|---|---|---|---|---|
| | | 0.2g | 0.8g | 1.6g |
| | 6 hours | 10.0 | 25.7 | 22.3 |

EXAMPLE 5

Example 1 was repeated except that proteose peptone was substituted for the peptone. The results are set forth in the table below:

TABLE 5

| Bacteria | Time | Count ($\times 10^7$ CFU/ml) | | |
|---|---|---|---|---|
| | | 0.2g | 0.8g | 1.6g |
| Escherichia coli | 0 hours | 2.2 | 1.78 | 1.9 |
| | 4 hours | 10.0 | 15.4 | 14.5 |
| | 5 hours | 7.4 | 22.0 | 22.0 |
| | 6 hours | 7.6 | 20.4 | 29.0 |
| Shigella sonnei | 0 hours | 6.9 | 6.38 | 4.6 |
| | 4 hours | 14.0 | 23.2 | 20.6 |
| | 5 hours | 13.4 | 20.8 | 28.8 |
| | 6 hours | 13.8 | 25.4 | 33.4 |
| Klebsiella pneumoniae | 0 hours | 4.1 | 3.52 | 3.5 |
| | 4 hours | 12.6 | 15.2 | 15.4 |
| | 5 hours | 12.8 | 26.0 | 23.4 |
| | 6 hours | 13.4 | 21.2 | 17.8 |
| Enterobacter cloacae | 0 hours | 4.2 | 0.8 | 4.3 |
| | 4 hours | 12.2 | 24.2 | 17.6 |
| | 5 hours | 13.0 | 28.3 | 27.0 |
| | 6 hours | — | 27.0 | 35.2 |
| Providencia species | 0 hours | 6.4 | 6.8 | 7.7 |
| | 4 hours | 19.2 | 33.2 | 32.0 |
| | 5 hours | 22.8 | 44.8 | 41.8 |
| | 6 hours | 24.6 | 49.6 | 44.6 |
| Proteus mirabilis | 0 hours | 5.6 | 5.98 | 5.3 |
| | 4 hours | 18.8 | 38.2 | 32.4 |
| | 5 hours | 18.8 | 38.2 | 38.0 |
| | 6 hours | 18.4 | 39.6 | 48.6 |
| Salmonella typhimurium | 0 hours | 3.0 | 3.86 | 5.0 |
| | 4 hours | 15.0 | 28.0 | 25.2 |
| | 5 hours | 15.0 | 34.2 | 30.6 |
| | 6 hours | 17.8 | 35.2 | 38.4 |
| Pseudomonas aeruginosa | 0 hours | 1.8 | 1.78 | 2.2 |
| | 4 hours | 5.4 | 7.98 | 11.3 |
| | 5 hours | 9.3 | 14.2 | 21.6 |
| | 6 hours | 8.7 | 15.8 | 19.0 |
| Citrobacter species | 0 hours | 4.4 | 3.82 | 5.2 |
| | 4 hours | 15.8 | 23.2 | 26.8 |
| | 5 hours | 16.6 | 27.6 | 28.2 |
| | 6 hours | 16.0 | 32.2 | 34.8 |
| Arizona | 0 hours | 2.5 | 1.92 | 2.7 |
| | 4 hours | 10.8 | 14.2 | 15.0 |
| | 5 hours | 11.2 | 22.4 | 17.8 |
| | 6 hours | 11.6 | 25.6 | 24.0 |
| Edwardsiella | 0 hours | 1.6 | 1.3 | 1.3 |
| | 4 hours | 3.6 | 5.9 | 10.3 |
| | 5 hours | 3.4 | 8.3 | 12.8 |
| | 6 hours | 3.9 | 10.0 | 15.8 |
| Yersinia | 0 hours | 6.4 | 3.0 | 5.9 |
| | 4 hours | 11.4 | 12.2 | 13.2 |
| | 5 hours | 13.4 | 18.0 | 19.6 |
| | 6 hours | 13.4 | 22.4 | 26.4 |
| Serratia marcescens | 0 hours | 9.9 | 6.14 | 6.5 |
| | 4 hours | 28.0 | 26.2 | 25.8 |
| | 5 hours | 27.6 | 30.2 | 27.6 |
| | 6 hours | 33.8 | 37.8 | 35.8 |
| Proteus vulgaris | 0 hours | 5.2 | 7.6 | 7.4 |
| | 4 hours | 12.6 | 19.6 | 18.4 |
| | 5 hours | 11.2 | 29.4 | 27.2 |
| | 6 hours | 13.6 | 33.2 | 33.6 |

EXAMPLE 6

In order to compare the medium of the present invention with the results obtained utilizing a standard broth growth technique, i.e., tryptic soy broth prior to placing the bacteria onto discs for use in the Kirby-Bauer procedure, 100 growing devices were prepared which contained the same medium as set forth in Example 1. One hundred clinical isolates of bacteria that were received from patients were run using both the growing device and the standard growing technique of the standard set forth for the Kirby-Bauer test. The bacteria tested included:

*Escherichia coli*
*Klebsiella pneumoniae*
*Pseudomonas aeruginosa*
*Acinetobacter calocoaceticus*
*Proteus mirabilis*
*Proteus morganii*
*Enterobacter aerogenes*
*Enterobacter cloacae*
*Serratia marcescens*
*Pasteurella* (species)
CDC Group II F
*Moraxella*
*Citrobacter freundii*

Specifically, 4 to 5 isolated colonies were touched with the wand from the growing device and the wand was used to inoculate the growing medium in the growing device. The units were incubated at 35° C. in a 3 M brand incubator Model 107 for 4 hours. The top tape seal was removed from the cap of the growing unit and 6 to 8 drops of bacterial suspension were dispensed onto a cotton swab. The swab was streaked in three directions over a Mueller-Hinton agar plate and the Kirby-Bauer test was completed according to the National Clinical Committee for Laboratory Standards (NCCLS) Antibiotics Susceptibility Standard set forth above. A comparison was made between the results obtained in respect to the susceptibility of the organism tested in using the growth media of the present invention versus the standard technique for growing bacteria. The results were comparable.

EXAMPLE 7

The following materials were dissolved in 1000 milliliters of deionized water and steam sterilized at 121° C. for 15 minutes:

1.7 gram Trypticase
0.3 gram Phytone
0.25 gram Dextrose
0.5 gram NaCl
0.25 gram $K_2HPO_4$ The growing devices utilized in this example were polypropylene sleeves as above described with the medium placed directly therein. The sleeves were capped with a plastic cap containing a "Tyvec" filter. The medium was inoculated using a wire loop with *Staphyloccocus aureus* bacteria obtained from 4 to 5 colonies of said bacteria on an agar plate. The growing devices were vortexed, i.e., mixed for 10 seconds and then incubated at 35° C. Viable bacteria counts were performed at 0, 1, 2½, 4½, 5½, 6½, 11½, 13½, 23½ and 31 hours. The results show that the count initially was $1 \times 10^4$ and at 11½ hours the count had increased to about 1.7 to $1.9 \times 10^8$ CFU/ml and did not substantially decrease therefrom through the remainder of the aforesaid time/count intervals.

What is claimed is:

1. An aqueous medium capable of growing at least one species from at least two different genera of aerobic, pathogenic, rapidly growing bacteria from a beginning population to a predetermined ending population of about $6 \times 10^7$ to $3 \times 10^8$ CFU/ml at which said growth of said bacteria substantially subsides due to the lack of nutrient in said medium and wherein said bacteria remain viable for at least 18 hours, said medium comprising an aqueous solution comprising about 0.42 to about 0.70 milligrams of carbon per milliliter of medium and about 0.09 to about 0.15 milligrams of nitrogen per milliliter of medium in the form in which said nutrients are present in peptone or about 0.16 to about 0.27 milligrams of carbon per milliliter of medium and about 0.035 to about 0.056 milligrams of nitrogen per milliliter of medium in the form in which said nutrients are present in proteose peptone and vitamins and minerals of sufficient quantity to provide said growth and in a form usable by said bacteria for said growth.

2. The medium of claim 1 wherein said medium comprises an aqueous solution of peptone which is buffered to maintain a pH of from about 7 to about 8.

3. The medium of claim 1 wherein said medium comprises an aqueous solution of proteose peptone which is buffered to maintain a pH of from about 7 to about 8.

4. An aqueous medium according to claim 1 wherein said medium comprises about:
- 0.8 parts by weight of peptone;
- 0.03 parts by weight of dextrose;
- 2.5 parts by weight of dipotassium phosphate;
- 1.25 parts by weight of monopotassium phosphate; and
- 5.0 parts by weight of sodium chloride.

* * * * *

UNITED STATES PATENT AND TRADEMARK OFFICE
CERTIFICATE OF CORRECTION

PATENT NO. : 4,250,264
DATED : February 10, 1981
INVENTOR(S) : Robert L. Nelson and James F. Drake It is certified that error appears in the above—identified patent and that said Letters Patent is hereby corrected as shown below:

Column 2, line 63, "visible" should read -- viable --.

Column 4, line 28, after "bacteria" insert -- desired and depending upon the type of bacteria --.

Column 7, line 27, "gram" should read -- grams --.

line 28, "gram" should read -- grams --.

Signed and Sealed this

Thirtieth Day of June 1981

[SEAL]

Attest:

RENE D. TEGTMEYER

Attesting Officer

Acting Commissioner of Patents and Trademarks